United States Patent [19]
Jeong et al.

[11] Patent Number: 5,903,351
[45] Date of Patent: May 11, 1999

[54] METHOD AND APPARATUS FOR SELECTIVE SPECTROSCOPIC ANALYSIS OF A WAFER SURFACE AND GAS PHASE ELEMENTS IN A REACTION CHAMBER

[75] Inventors: Sang Sup Jeong; Kyeong Koo Chi, both of Kyungki-do; Chan Ouk Jung, Seoul, all of Rep. of Korea

[73] Assignee: Samsung Electronics Co., Ltd., Suwon, Rep. of Korea

[21] Appl. No.: 08/946,168

[22] Filed: Oct. 7, 1997

[30] Foreign Application Priority Data

Nov. 13, 1996 [KR]  Rep. of Korea ..................... 96-53821

[51] Int. Cl.⁶ ....................................... G01B 9/02
[52] U.S. Cl. ............................ 356/346; 356/359
[58] Field of Search ...................... 356/359, 360

[56] References Cited

U.S. PATENT DOCUMENTS

| | | | |
|---|---|---|---|
| 3,850,526 | 11/1974 | Corey, III | 356/109 |
| 4,302,108 | 11/1981 | Timson | 356/359 |
| 5,563,707 | 10/1996 | Prass et al. | 356/361 |

OTHER PUBLICATIONS

Barbara J. Barner et al. "Polarization Modulation Fourier Transform Infrared Reflectance Measurements of Thin Films and Monolayers at Metal Surfaces Utilizing Real–Time Sampling Electronics,"; Anal. Chem. 1991, vol. 63, p. 55.

T.A. Cleland et al. "Detection of dry etching product species with in situ Fourier transform infrared spectroscopy,".

*Primary Examiner*—Robert Kim
*Assistant Examiner*—Andrew H. Lee
*Attorney, Agent, or Firm*—Jones, Volentine, Steinberg & Whitt, L.L.P.

[57] ABSTRACT

A spectroscopic analyzing method and apparatus for a wafer surface and gas phase elements in a reaction chamber. A beam of radiant energy is introduced from a light incident apparatus to the reaction chamber through a window on a wall of the reaction chamber at a predetermined, but variable, angle of incidence. The angle of incidence is set by adjusting optical elements in the light incident apparatus and an angle of the window. At one angle of incidence, the beam of radiant energy is caused to interact with gas-phase elements in the reaction chamber for spectroscopic analysis. At another angle of incidence, the beam of radiant energy is caused to interact with the wafer surface for spectroscopic analysis.

14 Claims, 2 Drawing Sheets

METHOD AND APPARATUS FOR SELECTIVE SPECTROSCOPIC ANALYSIS OF A WAFER SURFACE AND GAS PHASE ELEMENTS IN A REACTION CHAMBER

BACKGROUND OF THE INVENTION

1. Field of the Invention

The present invention relates to the general field of spectroscopic analysis, and more particularly, to the analysis of gas-phase materials and the surface of a wafer sample contained in a reaction chamber where beams of radiant energy are passed through the reaction chamber and caused to interact with the wafer sample or gas phase materials.

2. Description of the Related Art

The increased integration of semiconductor elements into electronic devices has prompted an increased need for lithography processes that are capable of achieving high aspect ratios and fine etching patterns. As a result, plasma etching processes for achieving high step difference, formation of fine patterns, and high anisotropic etching have gained in importance. In particular, processes for fabricating very large scale integrated devices, such as 256M DRAM's (Dynamic Random Access Memory) or more, require etching techniques that achieve high etching selectivity with respect to an underlying film, that minimize damage caused by plasma, and are capable of finely adjusting a pattern.

New plasma sources and new etching gases have been proposed in an effort to realize such an etching technique. In addition, research into ensuring optimal etching conditions through examination of etching reactions and appropriate control thereof is on-going.

Examination of the etching reactions involves in-situ analysis techniques for directly analyzing the wafer surface composition during a wafer etch process, observing behavior of adsorbing species, and analyzing the wafer surface chemical structure. However, current in-situ analysis techniques are ineffective because of the complexity of plasma and plasma disturbance, interference of surface discharge electrons caused by the plasma, and variation of energies.

Recent analysis techniques, including optical emission spectroscopy (OES) and laser induced fluorescence (LIF), have been proposed but these techniques can only analyze gas-phase plasma species. As such, there is a need for an analysis technique capable of directly analyzing the surface of a wafer as well as gas phase species during etching process.

SUMMARY OF THE INVENTION

The present invention is therefore directed to a method and apparatus for in-situ analysis of the surface of a wafer in a reaction chamber, as well as gaseous phase elements, using a radiant energy beam spectroscopic system which substantially overcomes one or more of the problems due to the limitations and disadvantages of the related art.

Generally, infrared spectroscopy has been utilized to analyze materials being processed during semiconductor manufacture. Two methods of infrared spectroscopy include a transmission absorption method and reflection method. In the transmission absorption method, a sample is analyzed by observing the change in intensity of an infrared radiation beam transmitted through the sample with a beam that is not transmitted through the sample. In the reflection method sample analysis is conducted through comparison (usually division) of beam intensity of a first beam incident upon a sample and a second beam reflected from a sample. In some cases, both methods are used. For example, with a sample having a thin surface, such as a material layer forming a thin film on a wafer or a material forming a surface adsorbing layer, analysis is performed using a combined method of absorption/reflection spectroscopy.

The present invention utilizes a modified reflection/absorption technique associated with the passage of radiant energy through a reaction chamber to analyze gas-phase species, e.g., a plasma in a reaction chamber, as well as the structural surface of a wafer in the reaction chamber.

To achieve these and other advantages, the present invention provides an apparatus for in-situ analysis of contained samples comprising an optical source, a reaction chamber, a plurality of incoming and outgoing optics, and a detector. The reaction chamber includes a first and second window positioned to receive and provide an exit, respectively, for a beam of incident radiation from the source. The first window is preselected and can be repositioned or replaced by the operator. The first window is selected according to the desired angle of incident light to analyze either the wafer surface or the gas phase elements in the reaction chamber.

In another aspect, the present invention provides a method for in-situ analysis of wafer samples and gas phase elements contained in a reaction chamber by selectively directing a beam of radiant energy at a desired angle within the reaction chamber. The method includes the steps of: producing a light beam; receiving the light beam and redirecting the light beam to a reaction chamber at an incident angle, such that the incident angle is adjustable to analyze either the wafer surface or gas phase elements in the reaction chamber; and receiving a reflected light beam from the reaction chamber and redirecting the reflected light beam to a detector element for spectroscopic analysis.

BRIEF DESCRIPTION OF THE DRAWINGS

The above objects and advantages of the present invention will be described with reference to the attached drawings in which.

DETAILED DESCRIPTION OF A PREFERRED EMBODIMENT

Figure 1:
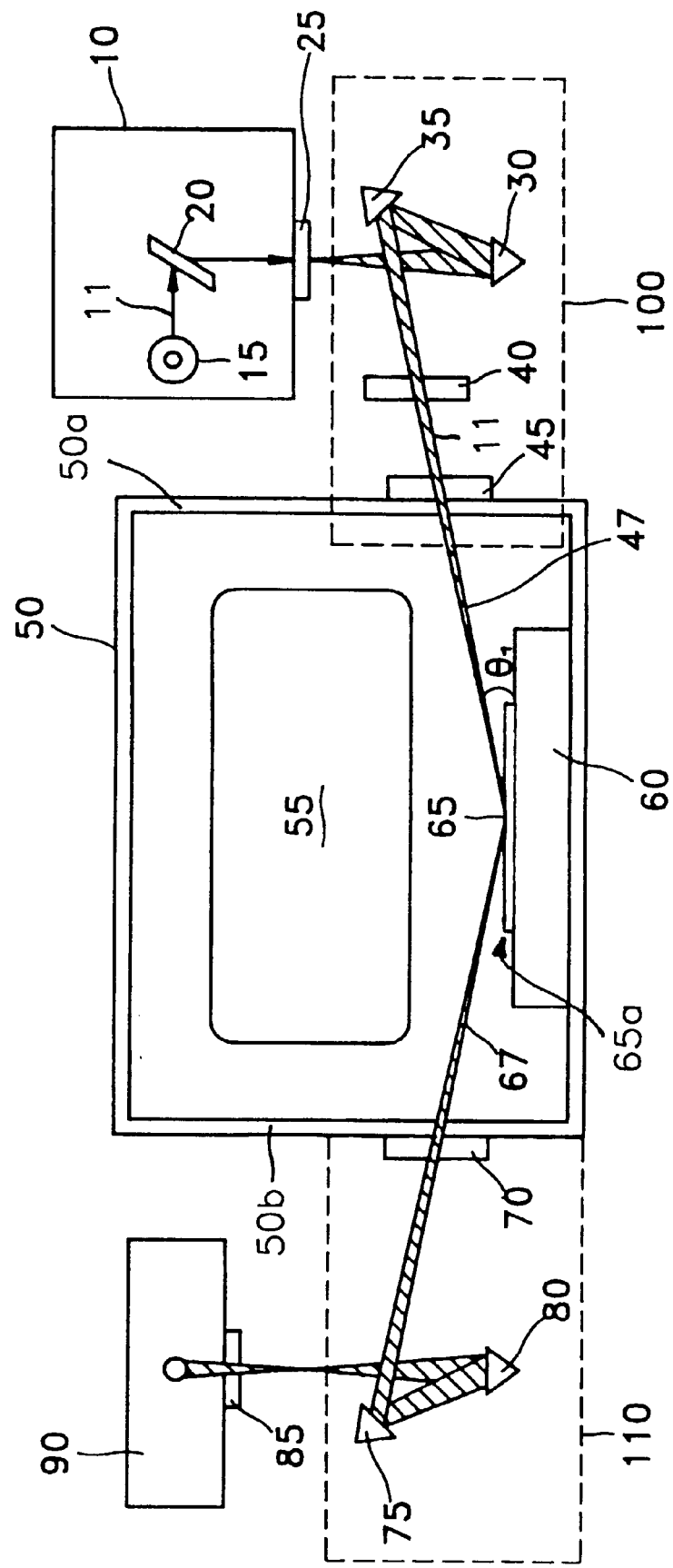
FIG. 1 is a schematic view of an apparatus according to the present invention.

A wafer surface and gas phase element analyzing apparatus according to the present invention will now be described along a sequential path of light with reference to FIG. 1. Interferometer 10 produces a preselected beam of radiant energy 11 at optical source 15. Beam 11 passes via beam splitter 20 to light transmitting window 25 positioned on the interferometer 10. The beam 11 passes through the light transmitting window 25 and is received and redirected by light incident apparatus 100.

The light incident apparatus 100 includes a plane mirror 30, curved surface mirror 35, and polarizer 40 that cooperate to direct the beam 11 through a light incident window 45, installed on an outerwall 50a of reaction chamber 50, thereby forming an incident beam 47. The composition of the light incident apparatus 100 will be described in greater detail later in the specification.

Returning to FIG. 1, incident beam 47 is shown incident upon an upper surface 65a of a wafer 65 at a predetermined incident angle $\theta_1$. Wafer 65 is positioned on top of a wafer supporter 60 within the reaction chamber 50.

A portion of incident beam 47 is absorbed by the surface 65a of wafer 65 and a portion of the beam is reflected, thereby forming reflected beam 67. The reflected beam 67 passes through another window 70 installed on an outerwall 50b of reaction chamber 50. The reflected beam 67 is then directed, via light outgoing apparatus 110, onto a spectroscopic detector 90. Light outgoing apparatus 110 includes curved surface mirror 75 and a plane mirror 80.

Detector 90 may be any means known to the skilled artisan for performing spectroscopic detection and analysis on radiant energy which was caused to interact with a sample. Detector 90 further includes window 85 through which reflected beam 67 passes prior to being incident upon a detector element. As such, detector 90 detects information about material properties of the surface 65a of the wafer 65 contained within the reflected beam 67, or as discussed later, material properties of gas phase elements 55.

Preferably, the incident angle $\theta_1$, of the incident beam 47 can be adjusted within a range of between 0° and 10° with respect to the surface 65a of the wafer 65. The incident angle $\theta_1$ is set by adjusting the disposition of the curved surface mirror 35. An incident angle $\theta_1$ greater than 10° results in a large 'skin depth' or absorption depth. As such, the absorption band of the surface adsorption layer becomes buried under the absorption band of the substrate so that division of the two absorption bands becomes difficult. In addition, the reflectivity of light is lowered and the intensity thereof is thus reduced so that information about the surface becomes difficult to obtain.

Figure 2:
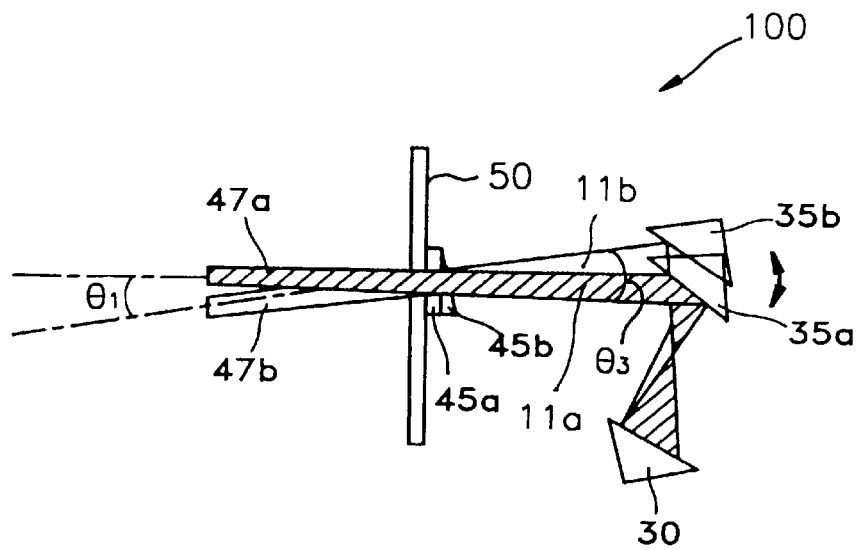
FIG. 2 is a schematic view of a light incident portion of the apparatus shown in FIG. 1.

FIG. 2 depicts light incident apparatus 100, wherein curved surface mirror 35 is shown in two different, but selectable, positions 35a and 35b. As discussed above, the different positions of curved surface mirror 35 are used to adjust an angle of incidence $\theta_1$ for the resulting incident beam 47 that passes into reaction chamber 50. Accordingly, the light beam 11a in the light incident apparatus 100 corresponds to mirror position 35a as depicted by the hatched line and results in first incident beam 47a. The light beam 11b corresponds to mirror position 35b as depicted by the clear line and results in second incident beam 47b. An additional mirror positioning control means (not shown) may be provided for manually or automatically adjusting the position of curved surface mirror 35.

The first incident beam 47a is created when the curved surface mirror 35 is in first position 35a, approximately perpendicular to a plane defined by the longitudinal axis of first incident window 45a. As a result, first incident beam 47a is directed into reaction chamber 50 approximately parallel to the upper surface 65a of the wafer 65 (see wafer 65 in FIG. 1). First incident beam 47a is used in the spectroscopic analysis of gas phase materials 55, e.g. plasma, etching gas, and the like, within reaction chamber 50. The first incident window 45a will be discussed later in greater detail with reference to FIG. 3A.

Returning to FIG. 2, second incident beam 47b is created when curved surface mirror 35 is in second position 35b, vertically displaced by an angle $\theta_3$ from first position 35a. As a result, second incident beam 47b would be incident upon the surface 65a of the wafer 65 at an angle $\theta_1$ of 0 to 10 degrees. As such, the material properties of the wafer surface 65a in the reaction chamber 50 can be analyzed.

When the curved surface mirror 35 is in the second position 35b, second incident window 45b is used in place of first incident window 45a. The second incident window 45b is oriented such that the lower end is displaced by a disposition angle $\theta_2$, measured from vertical as shown in FIG. 3B, which corresponds to the incident angle $\theta_1$ of incident beam 47b.

Regardless of whether the first incident window 45a or second incident window 45b is being used, in each case the incident beam 47a, 47b is controlled to be vertically incident, that is perpendicular or orthogonal, upon the respective incident windows 45a and 45b. If the incident beam is slantingly incident on the incident windows 45a and 45b, interference and attenuation can reduce the intensity of the light 67 reflected by the wafer surface 65a, or gas phase elements 55, thereby decreasing the effectiveness of the analysis being conducted. Therefore, it is important that the disposition states of the incident windows 45a and 45b be such that the respective incident beams 47a and 47b pass through the incident windows 45a and 45b in a vertical direction with respect to the planar surface of the incident windows.

Figure 3A:
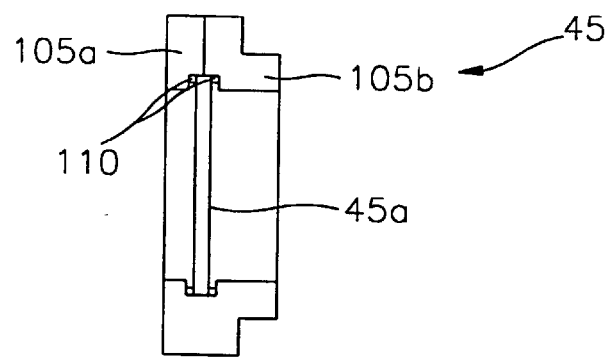
FIG. 3A is a side view of an embodiment of a window of the apparatus shown in FIG. 2.
Figure 3B:
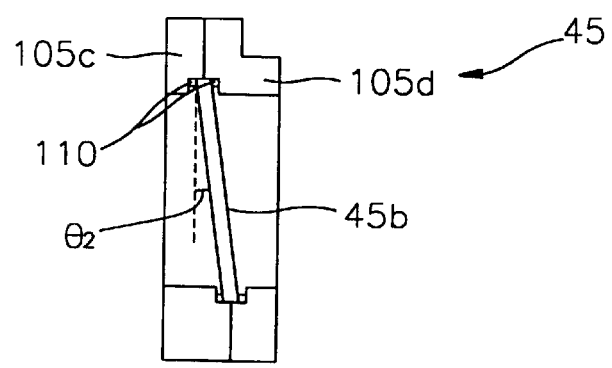
FIG. 3B is a side view of another embodiment of the window of the apparatus shown in FIG. 2.

FIG. 3A is a detailed side view of the first incident window 45a shown in FIG. 2, and FIG. 3B is a detailed side view of the second incident window 45b shown in FIG. 2. Common features of the two windows will first be described.

The first and second incident windows 45a, 45b are fixed and protected by first state flanges 105a and 105b and second state flanges 105c and 105d, respectively. An O-ring 110 is provided at the upper and lower ends where the first state flanges 105a and 105b and the first incident window 45a are connected. The O-ring 110 is also provided at the upper and lower ends where the second state flanges 105c and 105d and the second incident window 45b are connected. The O-ring 110 securely fixes the light incident windows 45a and 45b to the flanges 105a, 105b and 105c, 105d, respectively. Although the flanges 105a, 105b and 105c, 105d are separated into two parts as shown in FIG. 3A and FIG. 3B, the flanges may be formed as a single body.

Referring to FIG. 1 and FIG. 3A, the first incident window 45a is vertically disposed in the first state flanges 105a and 105b, and attached to the outerwall 50a of the reaction chamber 50 vertical to the upper surface 65a of the wafer 65 in the reaction chamber 50. Accordingly, light that is orthogonally incident upon the planar surface of the first incident window 45a travels parallel with the upper surface 65a of the wafer 65 in the reaction chamber 50 for analyzing the gas phase elements 55 in the internal space of the reaction chamber 50.

Referring to FIG. 1 and FIG. 3B, the lower end of the second window 45b is displaced by a disposition angle $\theta_2$, measured from vertical, within second flanges 105c and 105d. This disposition angle $\theta_2$ corresponds to the incident angle $\theta_1$ with respect to the upper surface 65a of the wafer 60 in the reaction chamber 50. Light that is orthogonally incident upon the planar surface of the second incident window 45b passes through the second window 45b in a "normal" direction and impacts the upper surface 65a of the wafer 65 in the reaction chamber 50 at the incident angle $\theta_1$. As described above, light is incident upon the wafer 65 in the reaction chamber 50 at a predetermined angle $\theta_1$ so that analysis of material properties of the wafer surface 65a are possible.

In each case, the disposition angle $\theta_2$ of the incidence windows 45a, 45b corresponds to the incident angle $\theta_1$ of the incident beam. The flanges housing one window with a first disposition angle can be replaced with flanges housing another window with another different disposition angle as needed.

The overall operation of the present invention will now be described with reference to all the Figures. Light beam 11, from optical source 15 of interferometer 10, is produced and directed towards beam splitter 20. Beam splitter 20 splits the beam 11 and directs same through window 25. The exiting beam is directed towards planar mirror 30 of light incident apparatus 100. Planar mirror 30 reflects the light beam 11 towards curved mirror 35, which redirects the light beam towards window 45 through polarizer 40. With the curved mirror 35 in position 35b (see FIG. 2), and the second incident window 45b (see FIG. 3B) being employed, the light beam passes through window 45b in the direction of wafer sample 65 accommodated on support 60. The light beam 47b is reflected off the wafer surface 65a in the direction of outgoing window 70. The reflected light beam 67 passes through outgoing light window 70, is reflected off curved mirror 75 and planar mirror 80, directed through window 85 and made incident upon detector 90. Detector 90 then performs spectroscopic analysis on the reflected light beam. This arrangement is used when analysis of the wafer surface 65a is desired.

In an alternate operation, with curved mirror 35 in position 35a (see FIG. 2), and the first incident window (see FIG. 3A) being employed, the light beam 47a will pass through the reaction chamber 50 without contacting the wafer surface 65a. Rather, the light beam 47a will absorb properties of gaseous phase elements 55 present in the chamber 50. The light beam 47a will still be made incident upon detector 90 by the cooperation of the above mentioned elements, namely, curved mirror 75, planar mirror 80 and window 85. By this alternate operation, spectroscopic analysis may be performed on gaseous phases elements 55 present in the reaction chamber.

While the invention has been described with reference to its preferred embodiment, it is understood that modifications to this embodiment and alternative embodiments may be effected by those skilled in the art without departing from the spirit and scope of this invention as herein below claimed. Specifically, it is understood that the invention may be equally applied to integrated circuit fabrication processes adopting other dry etching technologies, while remaining within the spirit and scope of the invention as claimed below.

What is claimed is:

1. An apparatus for analyzing a wafer surface and gas phase elements in a reaction chamber, comprising:
    an interferometer for producing a light beam;
    a light incident apparatus for receiving and redirecting said light beam to said reaction chamber at an incident angle, wherein said incident angle is adjustable to analyze one of said wafer surface and said gas phase elements in said reaction chamber; and
    a light outgoing apparatus for receiving a reflected light beam from said reaction chamber and redirecting said reflected light beam to a detector for analysis.

2. The apparatus of claim 1, said light incident apparatus comprising:
    a first mirror for receiving said light beam;
    a second mirror for redirecting said received light beam and providing said light beam to said reaction chamber at said incident angle, said second mirror being selectively positioned to thereby adjust said incident angle; and
    a light incident window attached to a predetermined position on a wall of said reaction chamber for allowing said light beam to pass into said reaction chamber to contact one of said wafer surface and said gas-phase elements in said reaction chamber.

3. The apparatus of claim 2, wherein a disposition angle of said light incident window, measured from a vertical plane coincident with said wall of said reaction chamber to a lower end of said light incident window, corresponds to said incident angle of said light beam, whereby said light beam impacts said light incident window at a substantially orthogonal angle.

4. The apparatus of claim 3, wherein said disposition angle of said light incident window is adjustable by replacing said light incident window having one disposition angle with a light incident window having another disposition angle.

5. The apparatus of claim 4, wherein said disposition angle of said light incident window and said incident angle are adjustable within a range of zero to ten degrees.

6. The apparatus of claim 5, wherein said disposition angle of said light incident window and said incident angle are adjusted such that said incident beam passes into and through said reaction chamber substantially parallel to said wafer surface.

7. The apparatus of claim 5, wherein said disposition angle of said light incident window and said incident angle are adjusted such that said incident beam passes into said reaction chamber and impacts said wafer surface.

8. A method for analyzing a wafer surface and gas-phase elements in a reaction chamber, the method comprising steps of:
    producing a light beam;
    receiving said light beam and redirecting said light beam to said reaction chamber at an incident angle, wherein said incident angle is adjustable to analyze one of said wafer surface and said gas phase elements in said reaction chamber; and
    receiving a reflected light beam from said reaction chamber and redirecting said reflected light beam to a detector element for analysis.

9. The method for analyzing a wafer surface and gas-phase elements in a reaction chamber according to claim 8, said step of receiving said light beam and redirecting said light beam further comprising steps of:
    selectively positioning a mirror for redirecting said received light beam and providing said light beam to said reaction chamber at said incident angle; and
    passing said light beam into said reaction chamber, through a light incident window attached to said reaction chamber, to contact one of said wafer surface and said gas phase elements in said reaction chamber.

10. The method for analyzing a wafer surface and gas-phase elements in a reaction chamber according to claim 9, said step of receiving said light beam and redirecting said light beam further comprising steps of:
    selecting a disposition angle of said light incident window corresponding to said incident angle of said light beam; and
    impacting said light beam on said light incident window at a substantially orthogonal angle.

11. The method for analyzing a wafer surface and gas-phase elements in a reaction chamber according to claim 10, wherein said step of selecting a disposition angle of said light incident window is performed by replacing said light incident window having one disposition angle with a light incident window having another disposition angle.

12. The method for analyzing a wafer surface and gas-phase elements in a reaction chamber according to claim 10, wherein said disposition angle and said incident angle are adjustable within a range of between zero and ten degrees during said step of receiving said light beam and redirecting said light beam.

13. The method for analyzing a wafer surface and gas-phase elements in a reaction chamber according to claim 12, wherein said disposition angle and said incident angle are adjusted such that said incident beam passes into and through said reaction chamber substantially parallel to said wafer surface during said step of receiving said light beam and redirecting said light beam.

14. The method for analyzing a wafer surface and gas-phase elements in a reaction chamber according to claim 12, wherein said disposition angle and said incident angle are adjusted such that said incident beam passes into said reaction chamber and impacts said wafer surface during said step of receiving said light beam and redirecting said light beam.

* * * * *